Figure 1:
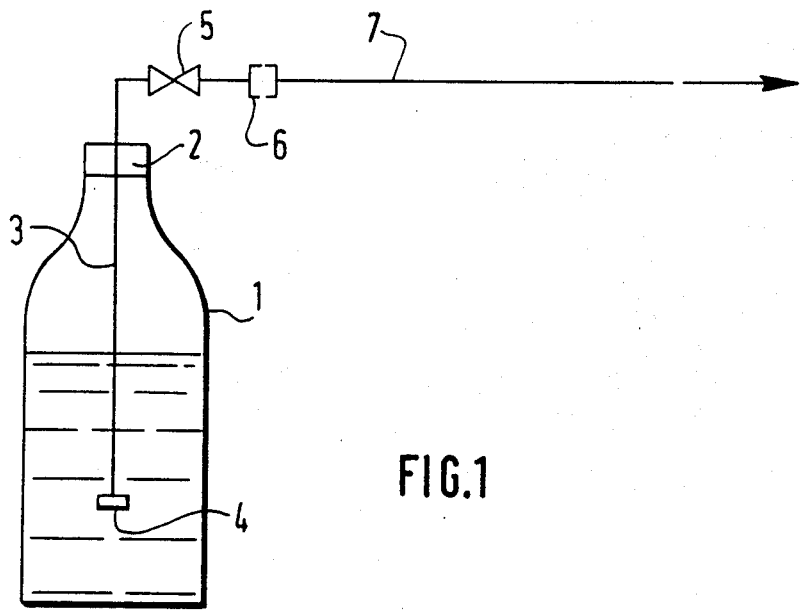

United States Patent [19]

Frejaville et al.

[11] Patent Number: 4,977,747
[45] Date of Patent: Dec. 18, 1990

[54] PROCESS AND CONTAINER FOR SUPPLYING SUPERCRITICAL $CO_2$

[75] Inventors: Serge Frejaville, Mejannes-Les-Ales; Philippe Mittelman, Fresnes; Claude Rajaonarivello, Nogent-sur-Marne; Jean-Michel Naud, Nanterre, all of France

[73] Assignee: L'Air Liquide, Society Anonyme pour l'Etude et l'Exploitation des Procedes Georges Claude, Paris, France

[21] Appl. No.: 404,452

[22] Filed: Sep. 8, 1989

[30] Foreign Application Priority Data

Sep. 8, 1989 [FR] France ............................ 88 11738

[51] Int. Cl.$^5$ .............................................. F17C 7/02
[52] U.S. Cl. ........................................ 62/50.1; 141/4; 141/9; 141/64
[58] Field of Search ................... 62/50.1; 141/4, 9, 63, 141/64

[56] References Cited

U.S. PATENT DOCUMENTS 2,482,778  9/1949  Joerren ................................ 62/46.1

FOREIGN PATENT DOCUMENTS 621019  4/1949  United Kingdom .

Primary Examiner—Ronald C. Capossela
Attorney, Agent, or Firm—Young & Thompson

[57] ABSTRACT

A cylinder (1) having a plunger tube (3) contains a mass of supercritical $CO_2$ containing 7 to 8% dissolved hydrogen, surmounted by a gaseous sky constituted by hydrogen under a pressure higher than about 120 bars. Supercritical $CO_2$ containing several percent of dissolved hydrogen can thus be obtained by merely opening the valve (5) of the cylinder. Used in the cosmetic industry.

10 Claims, 2 Drawing Sheets

PROCESS AND CONTAINER FOR SUPPLYING SUPERCRITICAL $CO_2$

The present invention relates to a process for supplying supercritical carbon dioxide, usable, for example, in the cosmetic industry as a solvent and propellant agent.

The current method for supplying supercritical carbon dioxide consists in employing a store of liquid carbon dioxide at $-20°$ C., at 20 bars, with a high pressure pump having several stages and a refrigerating unit, which is costly and complicated.

The document GB-A-621,019 proposed to provide, in a receptacle provided with withdrawing means, a charge of carbon dioxide surmounted by a gaseous charge under high pressure, so as to enable a rapid discharge at even every low temperatures, of the order of $-50°$ C. without however entailing excessive pressures at temperatures as high as $+60°$ C. The essential aim of such a charge in a receptacle according to this document is to provide a fire extinguishing system adapted to operate correctly at no matter what ambient temperature. To this end, there is selected a gas which remains gaseous even at very low temperature and the document recites the principal gases fulfilling this condition.

The present invention proposes to deliver supercritical carbon dioxide in a simple and economical way, and this object is attained in that the gaseous charge is constituted by hydrogen under a pressure higher than about 120 bars and in that said supply of supercritical carbon dioxide is effected by withdrawal while maintaining a charge of the gaseous hydrogen which is never below about 120 bars.

According to one embodiment, the gaseous hydrogen charge, initially at a pressure substantially higher than about 120 bars, is maintained in that condition during the supply of carbon dioxide, and all carbon dioxide withdrawal is stopped as soon as the pressure of said gaseous hydrogen charge is reduced by withdrawal of carbon dioxide to a value of about 120 bars and preferably, to avoid any possibility that the withdrawal pressure will fall below about 120 bars, the carbon dioxide is withdrawn through a plunger tube, the volume of the liquid carbon dioxide charge and the length of this tube being selected so that the pressure of the hydrogen will not fall below about 120 bars at the end of carbon dioxide withdrawal. The carbon dioxide could also be withdrawn through a conduit provided with a pressure controlling valve adjusted for automatic closing at any value of pressure lower than about 120 bars.

According to another embodiment, a charge of liquid carbon dioxide is introduced into a first pressure-resistant receptacle having fluid withdrawal means, the upper portion of this receptacle is placed in communication with an auxiliary receptacle containing hydrogen so as to supply hydrogen to the first receptacle under a pressure not lower than about 120 bars, and this communication is maintained during withdrawal of the carbon dioxide.

The invention also has as its object apparatus for storing and supplying supercritical carbon dioxide which comprises a receptacle having fluid withdrawal means with a charge of supercritical carbon dioxide containing about 7 to 8% dissolved hydrogen, surmounted by a gaseous sky constituted by hydrogen under a pressure higher than about 120 bars.

According to an embodiment, the pressure of the gaseous sky of hydrogen is about 160 bars at $+20°$ C.

According to another embodiment, the receptacle contains a withdrawal conduit provided with a pressure controlling valve that closes at any pressure lower than about 120 bars.

According to still another embodiment, the upper portion of the receptacle communicates with an auxiliary receptacle containing hydrogen under a pressure no lower than about 120 bars and preferably the two receptacles are connected by a conduit provided with a pressure reducer.

Figure 3:
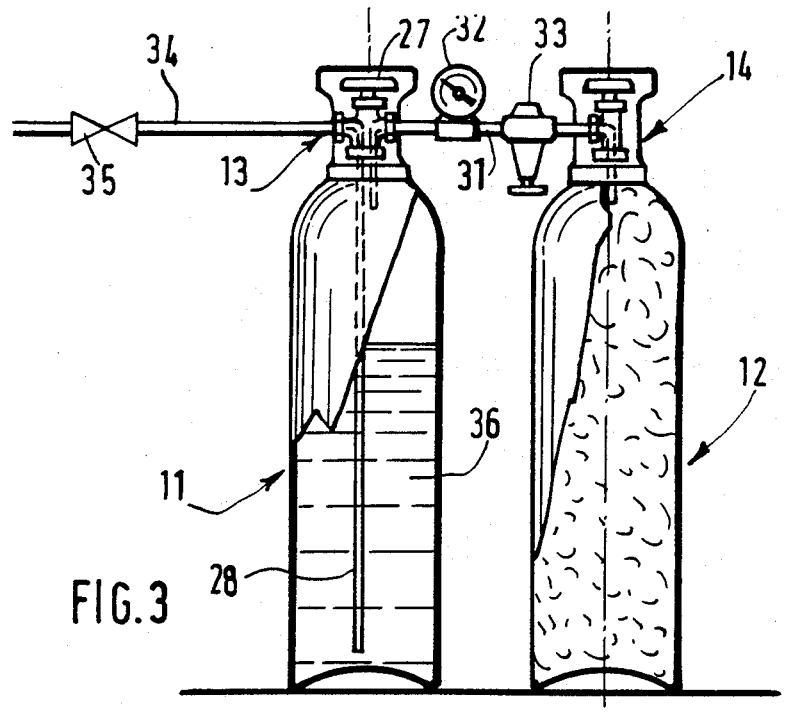
Figure 4:
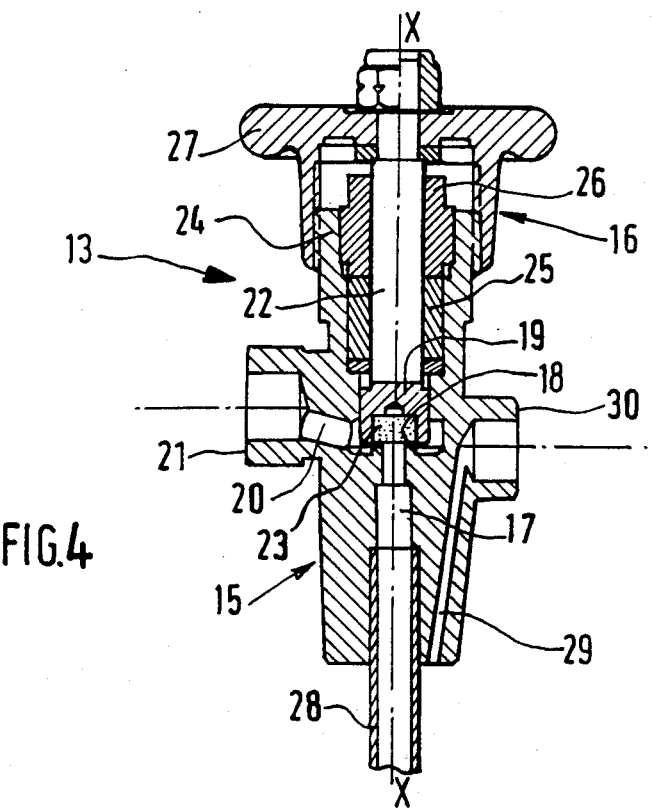

Examples of embodiment of the invention will now be described with respect to the accompanying drawings, in which:

FIGS. and 2 show two embodiments of the process according to the invention;

FIG. 3 is an elevational view, partially in section, of apparatus according to the invention; and FIG. 4 shows a longitudinal cross-section of a detail of the apparatus of FIG. 3.

There is shown in FIG. 1, in longitudinal cross-section, a steel cylinder 1, whose neck is provided with a plug 2 traversed by a plunger tube 3, which comprises at its lower end a calibrated orifice 4. The tube 3 descends to a level substantially above the bottom of the cylinder and which will be defined hereinafter.

Outside the cylinder, the tube 3 is provided with a stop valve 5 and terminates in a connection 6 for connecting a utilization conduit 7.

The cylinder 1 is filled in the following manner:

After having carried out a conventional preliminary treatment for cylinders adapted to receive very pure gases, liquid $CO_2$ from a supply at $-20°$ C., 20 bars, by means of a circulation pump and a reheater which brings it to about $0°$ C., for reasons related to the resilience of the steel of cylinder 1. The $CO_2$ has a purity of 99.998% and, by weighing the cylinder, a given quantity of it is measured. This quantity, which should be sufficient to immerse the calibrated orifice 4, corresponds for example to a volume of liquid equal to about half the volume of the cylinder.

One then lets the cylinder return to ambient temperature, which constitutes a stabilization phase of the $CO_2$ lasting at least two hours.

Then the cylinder is inverted, by any suitable handling means. The calibrated orifice 4 then emerges from the liquid and there is a delay for another stabilization phase of about 10 minutes, so that the liquid will be well assembled and the liquid-vapor equilibrium will be once more attained.

A high purity charge of hydrogen (less than 5 ppm water, less than 5 ppm oxygen) is then introduced through tube 3, until a pressure of about 160 bars is attained. This pressure is selected to be as high as possible but such that, for the maximum foreseeable ambient temperature (for example $+50°$ C.), it will remain below the service pressure of cylinder 1.

Finally, the cylinder is reinverted and, after a new stabilization period of about one hour, it is ready to supply supercritical $CO_2$ merely by opening valve 5.

The cylinder then is in the condition shown in FIG. 1, which is to say that it contains a charge constituted by:
 a mass of supercritical $CO_2$ containing a certain quantity of dissolved hydrogen, and
 a gaseous sky at about 160 bars, constituted solely of hydrogen.

Analyses have shown that when the pressure of the hydrogen falls from 160 bars to about 120 bars, the content of hydrogen dissolved in the liquid $CO_2$ is small and remains at a substantially constant value between 7 and 8%, while this content suddenly increases when the pressure falls below about 120 bars. As a result, if it is desired to withdraw only $CO_2$ of low hydrogen content, withdrawal will be stopped when the pressure, which drops with the lowering of the level of the $CO_2$, reaches a limit value not less than this value of about 120 bars.

To this end, as shown in FIG. 1, the tube 3 can be lowered no farther than a level corresponding to the volume of the gaseous sky which supplies the pressure of about 120 bars. If the filling volume of the liquid $CO_2$ is preselected, for example to be equal to about half the capacity of the cylinder as indicated above, the level in question can be determined by calculation. As a modification, if it is preferred to withdraw practically all the $CO_2$, the tube 3 will be lowered almost to the bottom of the cylinder, and the initial volume of liquid $CO_2$ will be calculated in a corresponding manner.

However, in both cases, the conduit 7 will conduct a gaseous $CO_2$-hydrogen mixture, or pure hydrogen, at the end of withdrawal. To avoid this, recourse can be had to the embodiment shown in FIG. 2: the cylinder containing initially about half its volume of $CO_2$, the tube 3 will descend almost to the bottom of the cylinder, and the utilization conduit 7 is provided with a pressure controlling valve 8 which closes when the pressure falls to the limit value of about 120 bars. The withdrawal thus stops automatically, and the cylinder is then changed.

There is shown in FIG. 3 apparatus constituted by two cylinders 11 and 12 of the same dimensions each provided with a valve 13, 14, respectively.

The valve 13, shown on a larger scale in FIG. 4, comprises a body 15, having a general axis X—X, and a manipulating device 16. The lower part of body 15, fixed in the neck of cylinder 11, defines an inlet conduit 17 which terminates in a seat 18 and opens into a chamber 19. A withdrawal conduit 20, which terminates in a principal connection 21, extends laterally from chamber 19, and this latter has an upper opening in which slides the lower end of the operating rod 22 of the valve, which is provided with a valve closure member 23 which can bear against seat 18.

The upper part of the body 15 comprises a tube 24 which is coaxial with rod 22. The operating device 16 comprises, in addition to rod 22, a sealing joint 25 which surrounds this rod and which is compressed in the tubing 24 by a packing nut 26, and an operating wheel 27 screwed on the upper end of the tube 24.

A plunger tube 28, which extends almost to the bottom of the cylinder 11, is fitted in the inlet conduit 17, and the lower part of the body 15 comprises an additional bore 29 which places the upper part of the cylinder in communication with an auxiliary lateral connection 30.

The valve 14 is identical to valve 13, except that its body has no bore 29 and auxiliary connection 30. Moreover, the cylinder 12 has no plunger tube, so that the inlet conduit 17 of valve 14 opens directly into the upper part of this cylinder.

As is seen in FIG. 3, the coupling 30 of valve 13 is connected to the coupling 21 of valve 14 by a conduit 31 provided with a manometer 32 and a pressure reducer 33. Moreover, a utilization conduit 34 provided with a stop valve 35 is connected to the coupling 21 of the cylinder II.

Figure 2:
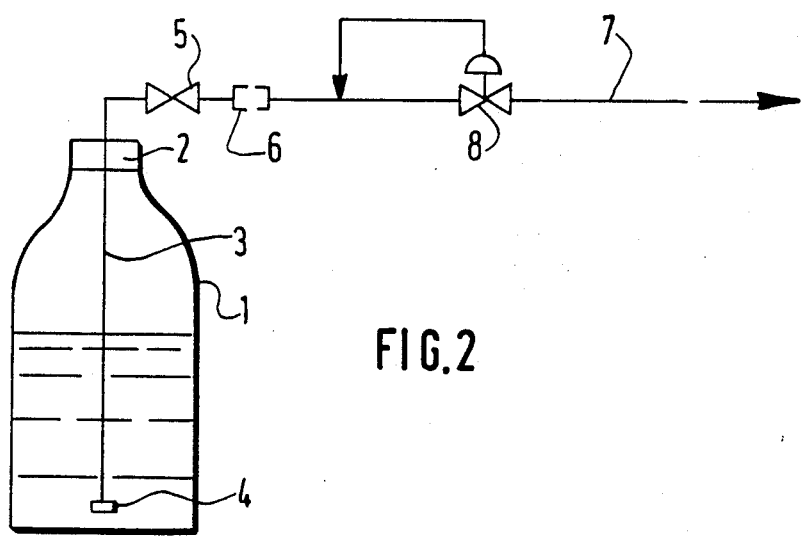

At the outset, the cylinder 12 contains hydrogen under a pressure substantially higher than 120 bars, for example 200 bars; the valve 14 is closed, and the cylinder 11 is filled to a predetermined level with liquid $CO_2$, in the manner described in connection with FIGS. 1 and 2, through the conduit 34.

Then, the valve 35 being closed, the pressure reducer 33 is adjusted to an outlet pressure P at least equal to about 120 bars, and valve 14 of cylinder 12 is opened. The $CO_2$ is thus raised to a pressure P and will be in supercritical state. The cylinder 11 then contains a mass 36 of supercritical $CO_2$ containing about 7 to 8% dissolved hydrogen, surmounted by a gaseous sky consisting only of hydrogen.

Supercritical $CO_2$ can then be withdrawn through the conduit 34, by opening valve 35. As the level of liquid $CO_2$ falls, the hydrogen passes from cylinder 12 to cylinder 11, and the latter remains constantly at the same pressure P. This remains true so long as the pressure in cylinder 12 remains higher than the value P; accordingly, by suitably choosing the initial level of liquid $CO_2$ in cylinder 11, all the $CO_2$ can be withdrawn under this same pressure P.

As a modification, pressure reducer 33 can be omitted. The $CO_2$ would then be delivered under a pressure progressively decreasing from the initial pressure prevailing in the cylinder 12.

What is claimed is:

1. A process for supplying supercritical carbon dioxide comprising the following steps:
   introducing into a container a quantity of liquid carbon dioxide at a first pressure
   introducing into said container high-purity hydrogen at a second pressure, superior to said first pressure and to 120 bars, thereby providing in said container supercritical carbon dioxide at said second pressure, containing less than 9% of dissolved hydrogen, surmounted by a gaseous charge of hydrogen
   selectively drawing off said carbon dioxide
   and discontinuing said carbon dioxide drawing off when the pressure in said container has fallen to a value not less than about 120 bars at ambient temperature.

2. The process of claim 1, wherein the carbon dioxide is drawn off through a conduit provided with a pressure controlled valve adapted to shut when the carbon dioxide pressure falls below said value.

3. The process of claim 1, which comprises the step of admitting into said container hydrogen at said second pressure from an auxiliary container when drawing off the carbon dioxide.

4. The process of claim 3, wherein the hydrogen is stored in said auxiliary container at a pressure greater than said second pressure.

5. The process of claim 1, wherein said second pressure is about 160 bars.

6. Apparatus for supplying supercritical carbon dioxide, which comprises a container having means for selectively drawing off fluid carbon dioxide therefrom, said container containing a mass of supercritical carbon dioxide containing about 7–8% of dissolved hydrogen and surmounted by a gaseous charge of hydrogen, the pressure in said container being higher than about 120 bars at ambient temperature, and means preventing drawing off of said carbon dioxide when the pressure in said container falls below about 120 bars at ambient temperature.

7. The apparatus of claim 6, wherein said pressure is about 160 bars.

8. The apparatus of claim 6, wherein said drawing off means includes a pressure controlled valve set to close at any pressure lower than about 120 bars at ambient temperature.

9. The apparatus of claim 6, comprising an auxiliary container containing hydrogen at a pressure higher than the pressure in said container containing carbon dioxide and in fluid connection with said container containing carbon dioxide.

10. The apparatus of claim 9, comprising a pressure reducer between said container and said auxiliary container.

* * * * *